United States Patent [19]

Tepperberg

[11] Patent Number: 4,705,030

[45] Date of Patent: Nov. 10, 1987

[54] HAND AUGMENTING SPINAL MANIPULATOR ENCIRCLING THE HAND

[76] Inventor: Phillip S. Tepperberg, 16900 NE. 5th Ct., North Miami Beach, Fla. 33162

[21] Appl. No.: 15,784

[22] Filed: Feb. 17, 1987

[51] Int. Cl.4 .......................... A61H 7/00; A61F 5/00; A61F 5/01

[52] U.S. Cl. ........................................ 128/69; 128/61; 128/67; D24/36

[58] Field of Search ........................ 128/69, 68, 44, 54, 128/60, 61, 67, 78, 24 R, 32; D24/36

[56] References Cited

U.S. PATENT DOCUMENTS

| | | | |
|---|---|---|---|
| D. 275,607 | 9/1984 | Blackman | D24/36 |
| 726,054 | 4/1903 | Hartford | 128/69 |
| 1,342,597 | 6/1920 | Post | 128/69 |
| 2,026,332 | 12/1935 | Walstrom | 128/69 |
| 2,063,818 | 12/1936 | Mankinen | 128/69 |
| 2,159,654 | 5/1939 | Catlin | 128/69 |
| 2,450,935 | 10/1948 | Carr | 128/24 R |
| 2,854,971 | 10/1958 | Williams | 128/69 |
| 4,126,129 | 11/1978 | Rainbow | 128/67 |
| 4,230,099 | 10/1980 | Richardson | 128/69 |
| 4,350,152 | 9/1982 | Strakowski | 128/24 R |
| 4,454,868 | 6/1984 | George | 128/67 |
| 4,483,328 | 11/1984 | Wolocko | 128/61 |
| 4,498,464 | 2/1985 | Morgan, Jr. | 128/61 |
| 4,590,926 | 5/1986 | Courtin | 128/67 |
| 4,611,581 | 9/1986 | Steffee | 128/69 |

FOREIGN PATENT DOCUMENTS

| | | | |
|---|---|---|---|
| 344528 | 11/1921 | Fed. Rep. of Germany | 128/60 |
| 7504998 | 11/1976 | Netherlands | 128/67 |
| 361599 | 11/1931 | United Kingdom | 128/54 |

*Primary Examiner*—Edgar S. Burr
*Assistant Examiner*—Tanya Lamb
*Attorney, Agent, or Firm*—Alvin S. Blum

[57] ABSTRACT

A device for treatment of anterior displacement of the vertebrae fits over the hand of the chiropractor. A groovein a first surface fits over the spinous processes and ridges parallel to the groove engage the transverse processes of the patient's vertebrae. The device is positioned immediately below the displaced vertebra and the patient is thrust backward. A second surface of the device engages the treatment table and arrests the backward motion of the normal vertebrae. The anteriorly displaced vertebra continues its backward motion, moving back into alignment with its neighbors. This manipulation is ordinarily performed against the chiropractor's bare hand. This device protects the hand from injury and enhances the performance of the treatment.

14 Claims, 8 Drawing Figures

HAND AUGMENTING SPINAL MANIPULATOR ENCIRCLING THE HAND

This invention relates to apparatus for straightening the spinal column by correcting the anterior displacement of one or more vertebrae and more particularly to apparatus slipped over the hand that is used as a fulcrum or stop by the chiropractor for this purpose that protects the hand from injury during the manipulation.

BACKGROUND OF THE INVENTION

U.S. Pat. No. 4,230,099 teaches a support curved to the normal shape of the spine with a longitudinal groove admitting the spinous processes and a pair of parallel elevations bordering the groove for engaging the transverse processes of the vertebrae.

When a person lies supine upon the support any misalignment of the vertebrae will, according to the inventor, be corrected without medical care or chiropractic manipulation.

In one type of misalignment of the vertebrae, to which the instant invention is directed, one or more vertebrae may be displaced anteriorly relative to adjacent vertebrae. When the displacement, or subluxation, involves many vertebrae, it may be referred to as Pottenger's Saucer because of the dish-like appearance of the back.

U.S. Pat. No. 4,611,581 teaches invasive, i.e. surgical, apparatus for correcting this condition by screws inserted into adjacent bones with pulling forces applied through a common plate that receives the screws and applies forces adjusted by nuts on the screws. The plate pulls the screw and the displaced vertebra in which it is inserted back into alignment with its normally positioned neighbors.

Chiropractors are taught a manipulation of the spine to non-invasively correct this condition. The chiropractor places his first hand on the patient's spine with the upper edge of the hand at the level of the normal vertebra immediately adjacent to the lowest anteriorly displaced vertebra. The chiropractor's second hand thrusts the patient's body weight toward the first hand in a thrusting motion directed backward (from chest to spine) and upward (from feet to head). The backward and upward motion of the spine is stopped by the first hand when it contacts the table on which the patient is lying supine. Because the hand is against the normally positioned vertebrae, but not the anteriorly displaced vertebrae, the motion of the displaced vertebra or vertebrae continue backward, moving back into normal alignment with the adjacent lower vertebrae. The thrust must be upward as well as backward because the facets, or meeting planes, between adjacent vertebrae are not at a ninety degree angle to the axis of the spine but extend upward at a lesser angle.

Each vertebra has a backward projecting, midline spinous process flanked on each side by a laterally projecting transverse process. When the patient is slender, the chiropractor uses the flat hand with the spine positioned between the heel of the hand engaging the transverse processes on a first side of the spinous processes and the metacarpal heads of the hand engaging the transverse processes on a second side of the spinous processes. For medium body types, the fingers are flexed to provide a higher fulcrum. For heavy body types, the hand must be closed into a fist with the spinous processes in the valley between the heel and the knuckles of the hand to be effective, otherwise the patient's flesh stops the thrust and no correcting forces are directed against the vertebrae.

The manipulation is generally performed on the treatment table, with the patient's back forced against the table. Alternatively, the patient may be upright and the back thrust against a wall. In either case the forces of the manipulation drive the vertebra or vertebrae back into position. Unfortunately, equal and opposite forces are applied to the hand of the chiropractor as it is used as a fulcrum or stop, compressed between the patient's back and the table or wall. This results in a variety of injuries to the chiropractors hand, including:

- arthritis
- avulsion fractures
- calcifications from chronic sprains and strains
- subluxations of hand and wrist
- carpal tunnel syndrome These injuries may prevent the chiropractor from practicing his profession. Furthermore, the chiropractor may deny the patient necessary treatment from fear of further injury to himself.

SUMMARY OF THE INVENTION

It is, accordingly an object of the invention to provide apparatus to be used by the chiropractor to perform these spinal manipulations for realignment of anteriorly displaced vertebrae without injury to his hand.

It is a further object to provide a device which enhances the chiropractor's ability to perform the necessary manipulations in a patient of any size.

The invention includes a device having provision for receiving the hand of the operator and a first surface for receiving the spine of the patient with a central longitudinal groove into which fit the spinous processes and parallel elevated surfaces adjacent said groove for engaging the transverse processes of the patient's vertebrae. The device includes a second surface for engaging an unyielding surface such as the treatment table or wall. The hand receiving portion lies between said first and second surfaces. The device is so constructed that the thrusting forces of the patient's body against said first surface are transmitted around the hand of the chiropractor to the second surface and from there to the unyielding surface to protect the hand from injury by those forces. The device is constructed with a curved second surface to enhance its proper functioning in the secondary motion following the primary thrust motion. The device may be constructed with a tail portion having greater flexibility than the head portion to provide a substantially rigid primary stop or fulcrum during the primary thrust motion and a more gentle action during the secondary motion.

DETAILED DESCRIPTION OF PREFERRED EMBODIMENT

Structure

Figure 7:
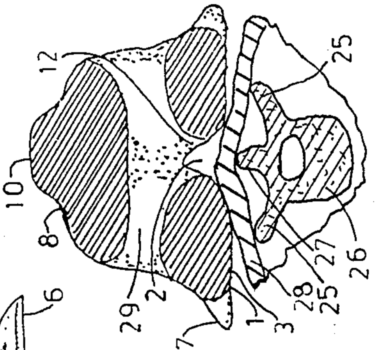
FIG. 7 is a cross section view taken on plane 7—7 of FIG. 1 with spine in place.

Referring first to FIGS. 1 through 6 which are various views of the same device, the embodiment comprises a one piece molded article including a first surface 1 having a longitudinal groove 2 extending from a head 4 to the start of the tail 6. The groove 2 is bordered on both sides by the ridges 3 extending from head 4 to merge together into tail 6 which flattens out wide to paravertebral elements 7. A second surface 8 has a longitudinal central ridge 10 extending from head to tail with anterior arc 9 and more gentle posterior arc 11. A hand receiving aperture 29 is located between the first and second surfaces. The central portion of the groove 2 in the first surface is open at its bottom, communicating with the hand receiving aperture 29 to form gap 12 (FIG. 7). A notch 5 is formed at the head 4 where the ridges 3 extend beyond the central groove 2. Immediately anteriorly to the notch 5, the curving first and second surfaces converge to form the anterior projections 31.

The device is preferrably formed of an elastomeric material as exemplified by polyurethane plastic. The anterior supports 13 of the first and second surfaces are thicker and the posterior supports 14 become progressively thinner toward the tail so that the tail is quite flexible and as one moves anteriorly the device is less flexible, being least flexible at the mass 30, while the anterior projections 31, having less thickness, is more flexible.

Operation

Figure 2:
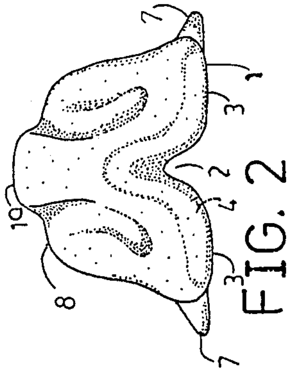
FIG. 2 is an anterior elevation view of the device.
Figure 3:
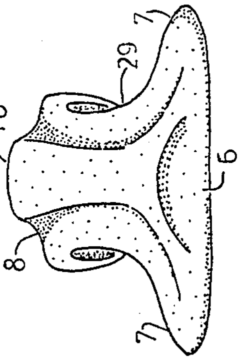
FIG. 3 is a posterior elevation view of the device.
Figure 1:
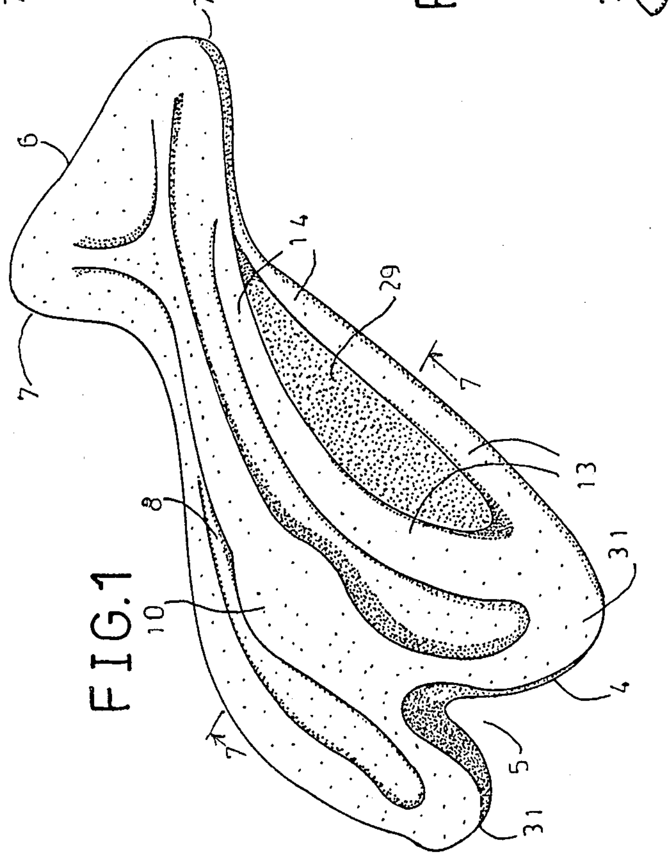
FIG. 1 is a perspective view of the device.
Figure 8:
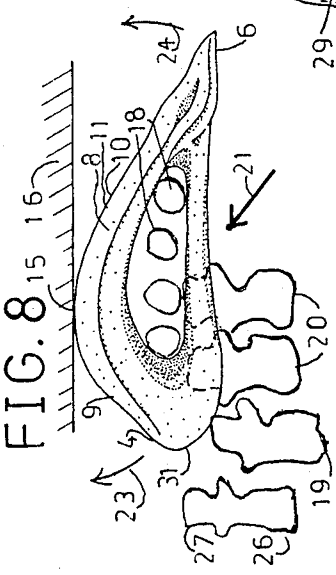
FIG. 8 is the view of FIG. 6 with outlines of vertebrae and fingers in position.
Figure 6:
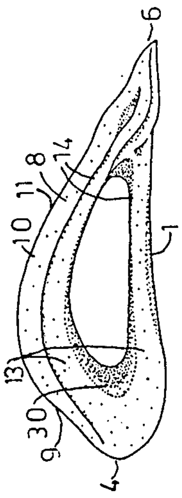
FIG. 6 is a side elevation view of the device.
Figure 4:
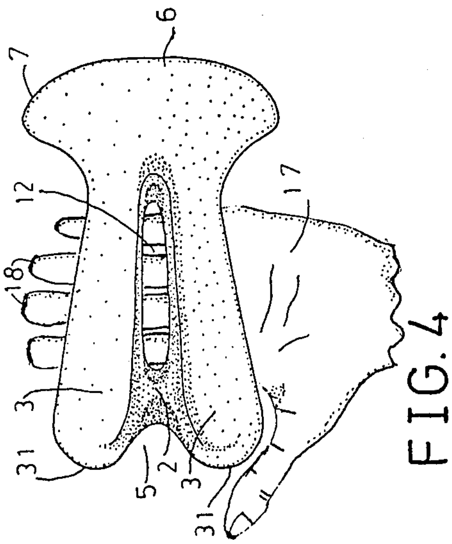
FIG. 4 is a top view of the device with hand in operating position.
Figure 5:
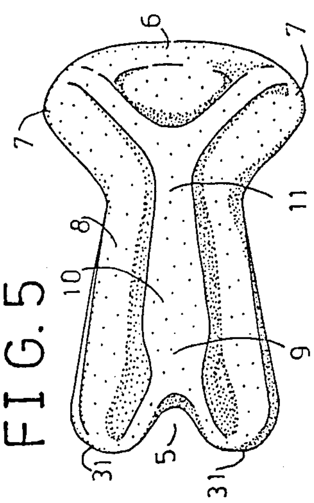
FIG. 5 is a bottom view of the device.

Referring now to FIGS. 4, 7 and 8, the hand 17 of the chiropractor fits into the hand receiving aperture 29 of the device with the palm toward the first surface 1. FIG. 7 is a cross sectional view taken on the plane 7—7 of FIG. 1 showing the device against the patient's vertebra in operating position. Each vertebra includes a thick vertebral body 26 with laterally projecting transverse processes 25 and a centrally projecting spinous process 27. The first surface 1 of the device is placed against the patient's back with the central longitudinal groove 2 aligned with and admitting the row of spinous processes and the two ridges 3 bordering the groove press against the rows of transverse processes with the soft tissue (skin and muscle) indicated by reference number 28 between the device and the bone. Along with the chiropractor's free hand, the operating hand's fingers 18 and thumb are available to palpate the back to ensure correct positioning. As shown in FIG. 8, the device is positioned with its head 4 toward the patient's head (cephelad). The normally aligned vertebrae 20 rest on first surface 1 with the lowest displaced vertebra 19 located at the curving anterior projection 31 and its spinous process is at the level of notch 5. In this position, the transverse processes of the normal vertebrae below the displaced vertebra are engaged by the ridges 3, but the transverse processes of the displaced vertebra 19 are not engaged. A single displaced vertebra is shown in FIG. 8. If more than one vertebra are displaced, the device would be similarly placed with respect to the normally aligned vertebrae.

With the device thusly positioned and held against the patient's back with the operator's first hand, his second hand applies a thrusting motion from the front (chest) of the patient, forcing the patient and the device against the treatment table 16 making contact between the second surface 10 and the table at contact point 15. The approximate direction of the thrusting motion is indicated by the arrow 21, being backward and cephelad to correspond with the angle of the facets between the vertebrae so that displaced vertebra 19 will continue its travel after the movement of the normal vertebrae 10 is arrested, moving at the correct angle back into alignment. The travel of normal vertebrae 20 is stopped by the contact of second surface 10 against table 16, because their transverse processes are pressed against the ridges 3 of first surface 1 and there is very little flexibility through the large solid mass 30. This mass 30 further prevents the hand receiving aperture 29 from collapsing, thereby transmitting the forces on surface 1 to the table 16 without crushing the operator's hand. The distance from point 15 to surface 1 is great enough to permit the manipulation of heavy body types and the durometer or flexibility of the plastic is selected to prevent collapsing by a heavy body. The anterior projections 31 of transverse process engaging ridges 3 curve upward and provide some flexibility so that the portion of the spine cephelad of the normal vertebrae is not forced against a hard square edge.

The thrust action may be divided into a first action when the thrust forces concentrate at the point of contact 15 of the second surface 10 with the table 16, and a second action wherein the body cephelad to the device continues its motion in the general direction of the arrow 21. This action causes the head 4 of the device to rotate in the general direction of arc 23 and the second surface 10 rolls against table 16 from contact point 15 along the anterior arc 9. This causes the flexible tail to be forced against the spine and it bends to relieve this force along the arc 24. Second surface 10 has a posterior arc portion 11 arranged so that the point of contact 15 will provide the correct angle for movement of the displaced vertebra back into alignment when the thrusting action is applied. The tail 6 has wide paravertebral extensions 7 to better anchor the device against the back during the motion. The central, longitudinal ridge 10 on second surface 8 is provided to better anchor the device against lateral motion when used with a slippery vinyl pad on the table.

The device is bilaterally symmetrical for use by either hand.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

What is claimed is:

1. A device intended for chiropractic treatment of the spine comprising:

a hand encircling means for receiving and protecting the open hand of an operator with the finger tips exposed on a first side of the device and the thumb and heel of said hand exposed on the opposite side of said device when said device is in operating position on said hand for treatment use;

an elongate first surface means on the exterior of said hand encircling means, extending from a head portion beyond the thumb side of the palm of said hand on a first end through a body portion over said palm to a tail portion beyond the opposite side of said palm on a second end, said first surface means including:

a. an elongate groove means extending from said head portion to said tail portion for receiving the spinous processes of the vertebrae of said spine when said first surface means is applied to said spine for said treatment;

b. elongate, transverse-process-engaging ridge means arranged on each of the two sides of said groove means for engaging the transverse processes of said vertebrae;

an elongate, arcuate, second surface means on the exterior of said hand encircling means extending from said head portion to said tail portion for engaging a solid treatment surface during said treatment while said first surface means is engaging said spine, said arcuate shape arranged to provide a tangential initial contact with said surface and a rolling contact progressing toward said head portion during the treatment motion.

2. In the device of claim 1, said tail portion having side extensions for projecting beyond both sides of said vertebrae to provide greater area of contact with said patient to anchor and maintain position during the treatment.

3. In the device of claim 1, said tail portion being thinner and more flexible than said body portion and said head portion to provide a yielding structure during said treatment motion.

4. In the device of claim 1, said second surface means including an elongate, central ridge means for maintaining position on said treatment surface during said treatment motion.

5. The device of claim 1, arranged with bilateral symmetry for use by either hand.

6. In the device of claim 1, said groove means having an elongate aperture in the base of said groove communicating with the opening for receiving said hand in said body portion.

7. The device of claim 1, formed of an elastomeric material and constructed with regions of different thicknesses so as to provide differential flexibility as required to provide greater rigidity at a region where initial forces are applied and more flexibility at regions where later forces are applied during a secondary rolling motion of said device on said treatment surface.

8. The device of claim 7 formed in a single molded part of an elastomeric plastic composition.

9. In the device of claim 1, said ridge means on said first surface means including an upwardly curving portion at said head portion.

10. In the device of claim 9, said ridge means on said first surface means terminating in anterior projections at said head portion.

11. In the device of claim 10, said anterior projections having greater flexibility than the adjacent portion.

12. A device for chiropractic manipulation of the spine, comprising:

an elongate first surface means for application against the spine of a patient, including a longitudinal groove means for receiving the spinous processes of said spine and a pair of parallel, elevated ridges, one on each side of said groove means for engaging the transverse processes of said vertebrae;

an elongate, curved, second surface means for engaging a stable treatment surface when a treatment thrust force is applied from the front of the patient, forcing said patient's spine against said device to arrest the backward motion of the vertebrae engaged by said ridges;

a hand-receiving aperture between said first surface means and said second surface means for passage of the fingers of the chiropractor's hand therethrough, said device thereby encircling said hand to protect it from injury by transmitting said force from said first surface around said hand to said second surface;

said first surface and said second surface converging at a head end and a tail end on either side of said aperture.

13. In the device of claim 12, said tail end terminating in a thin flat flexible portion.

14. The device of claim 13, molded of an elastomeric material, with increasing flexibility toward said tail end.

* * * * *